United States Patent
Shefer et al.

(10) Patent No.: US 7,053,034 B2
(45) Date of Patent: May 30, 2006

(54) TARGETED CONTROLLED DELIVERY COMPOSITIONS ACTIVATED BY CHANGES IN PH OR SALT CONCENTRATION

(75) Inventors: Adi Shefer, East Brunswick, NJ (US); Shmuel David Shefer, East Brunswick, NJ (US)

(73) Assignee: Salvona, LLC, Dayton, NJ (US)

( * ) Notice: Subject to any disclaimer, the term of this patent is extended or adjusted under 35 U.S.C. 154(b) by 180 days.

(21) Appl. No.: 10/119,567

(22) Filed: Apr. 10, 2002

(65) Prior Publication Data

US 2003/0195133 A1    Oct. 16, 2003

(51) Int. Cl.
*C11D 1/38*    (2006.01)
*C11D 3/50*    (2006.01)
*C11D 17/06*    (2006.01)

(52) U.S. Cl. ............ 510/349; 510/441; 510/101; 510/276; 510/504; 510/513; 510/515; 512/4

(58) Field of Classification Search .......... 510/441, 510/349, 101, 276, 515, 504, 513; 424/490, 424/491, 492, 493, 494, 496, 497, 498; 512/4
See application file for complete search history.

(56) References Cited

U.S. PATENT DOCUMENTS

| | | | |
|---|---|---|---|
| 3,686,025 A | 8/1972 | Morton | |
| 3,689,435 A | 9/1972 | Berni et al. | |
| 3,896,033 A | 7/1975 | Grimm, III | |
| 4,108,600 A * | 8/1978 | Wong ............ | 8/137 |
| 4,145,184 A | 3/1979 | Brain et al. | |
| 4,152,272 A | 5/1979 | Young | |
| 4,209,417 A | 6/1980 | Whyte | |
| 4,250,043 A | 2/1981 | Jones | |
| 4,339,356 A | 7/1982 | Whyte | |
| 4,402,856 A | 9/1983 | Schnoring et al. | |
| 4,434,086 A | 2/1984 | Hill et al. | |
| 4,446,032 A | 5/1984 | Munteanu et al. | |
| 4,464,271 A | 8/1984 | Munteanu et al. | |
| 4,476,041 A | 10/1984 | Hill et al. | |
| 4,488,973 A | 12/1984 | Hill et al. | |
| 4,536,315 A | 8/1985 | Ramachandran et al. | |
| 4,636,330 A | 1/1987 | Melville | |
| 4,842,761 A | 6/1989 | Rutherford | |

(Continued)

FOREIGN PATENT DOCUMENTS

AU    644357    12/1993

(Continued)

*Primary Examiner*—Lorna M. Douyon
(74) *Attorney, Agent, or Firm*—Mathews, Shepherd, McKay & Bruneau, P.A.

(57) ABSTRACT

The present invention relates to a novel controlled release carrier system for pH or salt triggered release and targeted delivery of fragrances and other active ingredients onto fabric, hair, skin, and other biological surfaces and which provides prolonged release of fragrances and other active ingredients over an extended period of time, or yields a high impact fragrance "burst" upon treating the target surface with heat (blow drying the hair, ironing the fabric). The controlled delivery system of the present invention is substantially a free-flowing powder formed of solid hydrophobic nano-spheres comprising the fragrance and other active ingredients that are encapsulated in a pH or salt sensitive micro-spheres. Also described are processes for preparing such compositions and processes for using same. Furthermore, certain components of the aforementioned compositions in combination with one another are novel, and other components have novel uses in increasing fragrance substantivity, particularly in fabric, hair, and skin care preparations. The invention further pertains to consumer and diversified products comprising the controlled release system of the present invention.

29 Claims, 1 Drawing Sheet

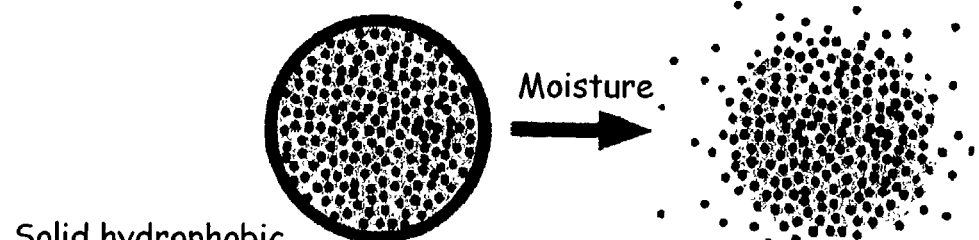

Solid hydrophobic nano-spheres encapsulated in a pH/salt sensitive micro-sphere

Solid hydrophobic nano-spheres

U.S. PATENT DOCUMENTS

| | | | |
|---|---|---|---|
| 4,919,841 A | 4/1990 | Kamel et al. | |
| 4,946,624 A | 8/1990 | Michael | |
| 4,954,285 A | 9/1990 | Wierenga et al. | |
| 4,973,422 A * | 11/1990 | Schmidt | 510/337 |
| 5,066,419 A | 11/1991 | Walley et al. | |
| 5,094,761 A | 3/1992 | Trinh et al. | |
| 5,102,564 A | 4/1992 | Gardlik et al. | |
| 5,112,688 A | 5/1992 | Michael | |
| 5,126,061 A | 6/1992 | Michael | |
| 5,137,646 A | 8/1992 | Schmidt et al. | |
| 5,154,842 A | 10/1992 | Walley et al. | |
| 5,188,753 A | 2/1993 | Schmidt et al. | |
| 5,207,933 A | 5/1993 | Trinh et al. | |
| 5,232,612 A | 8/1993 | Trinh et al. | |
| 5,232,613 A | 8/1993 | Bacon et al. | |
| 5,234,610 A | 8/1993 | Gardlik et al. | |
| 5,234,611 A | 8/1993 | Trinh et al. | |
| 5,236,615 A | 8/1993 | Trinh et al. | |
| 5,246,603 A | 9/1993 | Tsaur et al. | |
| 5,281,355 A | 1/1994 | Tsaur et al. | |
| 5,288,423 A | 2/1994 | Behan et al. | |
| 5,290,459 A | 3/1994 | Puentes-Bravo et al. | |
| 5,324,444 A | 6/1994 | Berry et al. | |
| 5,352,461 A * | 10/1994 | Feldstein et al. | 424/493 |
| 5,385,959 A | 1/1995 | Tsaur et al. | |
| 5,425,887 A | 6/1995 | Lam et al. | |
| 5,444,113 A | 8/1995 | Sinclair et al. | |
| 5,453,216 A * | 9/1995 | Kellett | 510/220 |
| 5,476,660 A | 12/1995 | Somasundaran et al. | |
| 5,506,201 A | 4/1996 | McDermott et al. | |
| 5,508,259 A | 4/1996 | Holzner et al. | |
| 5,543,157 A | 8/1996 | Trinh et al. | |
| 5,562,847 A | 10/1996 | Waite et al. | |
| 5,648,328 A | 7/1997 | Angell et al. | |
| 5,652,206 A | 7/1997 | Bacon et al. | |
| 5,656,584 A | 8/1997 | Angell et al. | |
| 5,668,097 A | 9/1997 | Trinh et al. | |
| 5,691,303 A | 11/1997 | Pan et al. | |
| 5,814,592 A | 9/1998 | Kahn et al. | |
| 5,840,668 A | 11/1998 | Behan et al. | |
| 5,851,452 A * | 12/1998 | Vallet Mas et al. | 264/4.6 |
| 5,858,959 A | 1/1999 | Surutzidis et al. | |
| 5,955,419 A | 9/1999 | Barket, Jr. et al. | |
| 6,022,501 A | 2/2000 | Dexter et al. | |
| 6,024,943 A | 2/2000 | Ness et al. | |
| 6,025,319 A | 2/2000 | Surutzidis et al. | |
| 6,042,792 A * | 3/2000 | Shefer et al. | 422/259 |
| 6,048,830 A | 4/2000 | Gallon et al. | |
| 6,051,540 A | 4/2000 | Shefer et al. | |
| 6,083,899 A | 7/2000 | Baker et al. | |
| 6,093,691 A | 7/2000 | Sivik et al. | |
| 6,228,398 B1 | 5/2001 | Devane et al. | |
| 6,379,683 B1 * | 4/2002 | Simonnet et al. | 424/401 |
| 6,395,302 B1 | 5/2002 | Hennink et al. | 424/489 |
| 6,531,444 B1 * | 3/2003 | Shefer et al. | 510/519 |
| 6,565,872 B1 * | 5/2003 | Wu et al. | 424/426 |
| 6,579,838 B1 | 6/2003 | Housmekerides et al. | |
| 6,589,562 B1 | 7/2003 | Shefer et al. | |
| 6,602,524 B1 * | 8/2003 | Batich et al. | 424/489 |
| 6,607,994 B1 * | 8/2003 | Soane | 442/59 |
| 6,616,946 B1 * | 9/2003 | Meier et al. | 424/489 |
| 6,632,671 B1 * | 10/2003 | Unger | 435/455 |

FOREIGN PATENT DOCUMENTS

| | | |
|---|---|---|
| EP | 0 334 490 A2 | 9/1989 |
| EP | 0 334 490 B1 | 9/1989 |
| EP | 0 382 464 | 6/1990 |
| EP | 0 376 285 A2 | 7/1990 |
| EP | 0382464 A2 * | 8/1990 |
| EP | 0 539 025 A2 | 4/1993 |
| EP | 0 469 228 B1 | 5/1996 |
| EP | 0 764 717 A1 | 3/1997 |
| EP | 0 908 174 A2 | 4/1999 |
| EP | 0 925 776 A2 | 6/1999 |
| WO | WO 93/05136 | 3/1993 |
| WO | WO 93/05137 | 3/1993 |
| WO | WO 93/05139 | 3/1993 |
| WO | WO 93/05141 | 3/1993 |
| WO | WO 93/13195 | 7/1993 |
| WO | WO 94/19448 | 9/1994 |
| WO | WO 94/28107 | 12/1994 |
| WO | WO 97/11152 | 3/1997 |
| WO | WO 97/34981 | 9/1997 |
| WO | WO 97/47720 | 12/1997 |
| WO | WO 98/12298 | 3/1998 |

* cited by examiner

Solid hydrophobic nano-spheres encapsulated in a pH/salt sensitive micro-sphere

Moisture →

Solid hydrophobic nano-spheres

FIG. 1

TARGETED CONTROLLED DELIVERY COMPOSITIONS ACTIVATED BY CHANGES IN PH OR SALT CONCENTRATION

BACKGROUND OF THE INVENTION

1. Field of the Invention

The present invention relates to a novel controlled release carrier system for targeted delivery of fragrances, as well as active ingredients, onto fabric, hair, skin, and other biological surfaces that is activated by changes in pH or salt concentration in the system proximate environment, and which provides prolong release of fragrances and other active ingredients over an extended period of time, or yields a high impact fragrance "burst" upon treating the target surface with heat, such as blow drying the hair or ironing the fabric.

2. Description of the Related Art

The household and cosmetic industry has searched for many years for ways to enhance the performance of consumer and diversified products and make them more aesthetically pleasing for the consumers. Consumer acceptance of consumer and diversified products is determined not only by the performance achieved with these products but the aesthetics associated therewith. Fragrance is an important aspect of the successful consumer and diversified products. Fragrances are being utilized, in addition to imparting an aesthetically pleasing odor, to convey to the consumer the product performance and effectiveness (i.e., the hair or the fabric is clean, freshly washed, etc.).

Fragrances are typically added to consumer and diversified products to convey to the consumer the product performance, i.e., provide a fresh, clean impression for these products as well as to surface treat these products. While the fragrance does not add to the performance of consumer and diversified products, it does make these products more aesthetically pleasing and the consumer has come to expect such products to have a pleasing odor. The fragrance plays a major, and often determining, role for the consumer in selecting and purchasing consumer and diversified products. Consumers are becoming increasingly educated and expect a high level of sophistication in their products. Many consumers would prefer for the fragrance, present in these products, to be deposited on the target surface (fabric, skin, hair) and remain there for an extended period of time to convey a lasting impression of freshness. Consumers are also interested in consumer and diversified products that deposit high level of fragrance onto the treated surfaces and release the fragrance upon heat treatment (ironing, blow drying the hair, etc.). Fragrance creation for consumer and diversified products is restricted not only by considerations such as availability and cost, but also by compatibility of the fragrance ingredients with other components in the product composition and the ability of the fragrance ingredients to deposit onto the target surface and survive the wash and rise process. Furthermore, a large amount of fragrance is being lost. Practice has shown that when currently available fabric care products are used, a large fraction of the fragrance is lost during the rinse process due to the solubility of certain fragrance ingredients in aqueous washing compositions, and the fraction of the fragrance which was deposited, quickly evaporates, due to the volatility of fragrance ingredients.

Typical fabric care products such as laundry detergent compositions and fabric softener compositions contain 0.5% to 1% by weight fragrance in their formulations. U.S. Pat. No. 6,051,540, issued to the inventor of this disclosure, discloses that in the course of the washing process wherein clothes are washed with the standard powdered laundry detergent, or fabric softener rinse, a very small fraction of the fragrance that is contained in these fabric care products is actually transferred to the clothes. Tests are described showing that the amount of fragrance that is left as a residue on the clothes can be as low as 1% of the original small amount of fragrance that is contained in these products formulation itself.

Attempts have been made to increase fragrance deposition onto fabric, hair, and skin and to hinder or delay the release of the fragrance so that the treated surface remains aesthetically pleasing for a prolonged length of time. Publications in the prior art indicate attempts to fulfill the foregoing needs.

The pH conditions as well as salt concentration in the various laundry cycles are markedly different, for example, the pH of the wash solution is 9–12 whereas the pH of the rinse water is neutral (pH 7). Differences in pH or salt concentration can also be found in the process of washing the hair with a shampoos or in the process of washing the skin with soaps or shower gels. These differences in pH and salt concentration can be utilized to protect fragrances and other active ingredients, during the wash cycle and deliver them during the rinse cycle under conditions that are more favorable for the deposition of fragrances and other active ingredients.

The prior art of which applicant is aware does not set forth a targeted controlled delivery system that is activated by pH or salt concentration in the system environment that can be incorporated in consumer and diversified products (i.e., fabric care, hair care, and skin care products) to enhance fragrance deposition and other active ingredients onto target surfaces such as, fabric, hair, skin, and other biological surfaces.

It is desirable to provide a method using an efficient and economical process for site-specific targeted delivery of a broad range of fragrances, and fragrance ingredients and other active ingredients onto fabric, hair, skin, and other biological surfaces that is triggered by pH or salt concentration, and prolong the release of fragrances and other active ingredients onto the target site.

SUMMARY OF THE INVENTION

The present invention relates to a novel controlled release carrier system for targeted delivery of fragrances and other active ingredients onto fabric, hair, and skin that is activated by changes in pH or salt concentration in the system proximate environment, and which provides prolonged release of fragrance and other active ingredients over an extended period of time, or yields a high impact fragrance "burst" upon treating the target surface with heat, such as blow drying the hair or ironing the fabric. More particularly, the invention relates to a controlled release system comprising of solid hydrophobic nano-spheres encapsulated in a pH or salt sensitive micro-spheres. The fragrance and other active ingredients can be incorporated in the hydrophobic nano-spheres, in the pH and salt sensitive micro-spheres, or in both the nano and micro-spheres.

The active ingredients and the nano-spheres are released from the micro-sphere when the pH or salt concentration of the surrounding environment reaches a desired level. This method of controlled release ensures that the fragrance and other active ingredients are delivered to a specific site and delivered only when the need for the active agent arises, or under conditions that ease deposition of the fragrance on the target site. Upon changes in pH or salt concentration, the micro-sphere pH or salt sensitive matrix material dissolves or swells. The dissolution or swelling of the matrix disrupts the micro-sphere structure and facilitates the release of the nano-spheres, fragrances, and other active ingredients.

The deposition of the nano-spheres of this invention onto the target surface is improved by optimizing particle size to ensure entrainment of the particles within target surface and maximize ionic interaction between the particles and the target surface.

With respect to the ionic interaction between the particles and the target surface, various charge groups can be incorporated in the nano-spheres structure, depending on the target surface, by incorporating a surface-active agent in the nano-spheres hydrophobic matrix. A cationic surface active agent will create positively charged nano-spheres; an anionic surface active agent will create negatively charged nano-spheres; a nonionic surface active will create neutral charged nano-spheres; and a zwitterionic surface active agent will create a variable charged nano-spheres.

In one embodiment, the nano-spheres of the present invention have high cationic charge density. High cationic charge density on the nano-sphere surface can be created by incorporating a cationic surface active agent into the solid hydrophobic matrix of the nano-spheres, by incorporating a cationic charge "booster" in the pH or salt sensitive microsphere matrix, or by using a cationic surface active agent in the nano-sphere matrix in conjunction with a cationic charge "booster" in the micro-sphere matrix.

In one embodiment, the present invention provides an improved carrier system for fabric care, hair care, skin care, and other consumer and diversified products, that has improved fragrance substantivity to bring the fragrance onto the target surface which have been treated with consumer and diversified products comprising the carrier system of the present invention. In the consumer and diversified product industry, the term "substantivity" refers to the deposition of the fragrance on the target surface (fabric, hair, skin, etc.) and the retention and perception of the fragrance on the target surface. The fragrance-carrier system also provides prolonged fragrance release from the target surface over an extended period of time, or yields a high impact fragrance "burst" upon treating the target surface with heat (blow drying the hair, ironing the fabric, etc.). In addition, the production of the fragrance-carrier system utilizes minimum processing steps and is efficient and economical.

The carrier system of the present invention can comprise a free-flowing, powder formed of solid hydrophobic nano-spheres comprising various active ingredients, as well as fragrances, that are encapsulated in a pH or salt sensitive micro-spheres, having the advantages of:

(i) protection of the active ingredients, as well as the volatile constituents of the fragrance, during storage, until needed;

(ii) pH or salt triggered release of the first said active ingredient and the nano-spheres comprising the second said active ingredient in response to change in pH or salt concentration in the system proximate environment (during the laundry rinse cycle, upon rinsing the hair, etc.), and, (iii) enhanced deposition of fragrances, as well as other active ingredients, onto the target surface (fabric, hair, skin);

(iv) prolonged release of fragrances, as well as other active ingredients, over an extended period of time; or (v) yield high impact fragrance "burst" upon treating the target surface with heat (blow drying the hair, ironing the fabric, etc.).

The invention also provides a method for producing the multi component controlled release system of the present invention including active ingredients that comprises the steps of:

(i) incorporating the active ingredients into the solid hydrophobic nano-spheres;

(ii) forming an aqueous mixture comprising of one or more active agents, the nano-spheres, and a pH or salt sensitive materials; and (iii) spray drying the mixture to form a dry powder composition.

The invention further provides a process for producing the multi component controlled release system including the active ingredients and the fragrance that comprises the steps of:

(i) heating hydrophobic materials to a temperature above the melting point of the materials to form a melt;

(ii) dissolving or dispersing the fragrance and a first active agent into the melt;

(iii) dissolving or dispersing a second active agent, and pH or salt sensitive materials, in the aqueous phase;

(iv) heating the composition to above the melting temperature of the hydrophobic materials;

(v) mixing the hot melt with the aqueous phase to form a dispersion;

(vi) high shear homogenization of the dispersion at a temperature above the melting temperature until a homogeneous fine dispersion is obtained having a sphere size of from about 1 micron to about 2 microns;

(vii) cooling the dispersion to ambient temperature; and (viii) spray drying the emulsified mixed suspension to form a dry powder composition.

The incorporation of spray dried nano-spheres comprising fragrances and other active ingredients encapsulated within a pH or salt sensitive matrix in consumer and diversified products, such as fabric care, hair care, skin care, and other consumer and diversified products has been found to enhance fragrance deposition onto the target site, and to extend the release rate of these fragrances and the active ingredients over an extended period of time.

The invention also provides consumer and diversified products comprising the multi component controlled release system of the present invention. Fabric, hair, and skin treated with products comprising the multi component controlled release system of the present invention were observed to exhibit high level of fragrance (high odor intensity) in both the wet and the dry state and fragrance perception has been observed to be perceived over an extended period of time, such as a few days to a few weeks, depending on the application and the type consumer product.

The present invention addresses the foregoing need to increase the deposition of wide range of active ingredients, as well as fragrances, onto target surfaces and prolong their release for an extended period of time by employing an advanced carrier system to bring the fragrances, as well as the other active ingredients, onto the target site.

Cationic charge groups on the nano-spheres surface can become associated, in use of the composition, with the fabric, hair, and skin and assists in adhering the nano-spheres onto target surface through both sphere entrainment and electrostatic interactions to effectively deliver fragrances and other active ingredients onto the target site and sustain their release rate. The hydrophobic matrix sustains the diffusion rate of the fragrances, as well as other active ingredients, through the nano-spheres and enables them to be released from the target site over an extended period of time, or during heat treatment such as ironing the fabric or blow drying the hair.

The multi-component controlled release system of the present invention can comprises from about 1% to about 50% by weight hydrophobic matrix, from about 1% to about 50% by weight pH or salt sensitive matrix, from about 0% to about 10% by weight cationic charge booster, from about 0% to about 20% by weight surface active agents, and from about 1% to about 50% by weight fragrance and other active ingredients. The micro-sphere has an average sphere size in the range from about 20 microns to about 100 microns, the nano-sphere have an average sphere size in the range from about 0.01 micron to about 5 microns and having a melting point in the range from about 30 degrees C. to about 90 degrees C. The micro-spheres can be incorporated into any consumer and diversified products, preferably in fabric care, hair care, and skin care products.

The additional components are usually present in an amount from about 1% to about 20% by weight of the spheres. The invention will be more fully described by reference to the following drawings:

BRIEF DESCRIPTION OF THE DRAWINGS

FIG. 1 is a schematic diagram of a controlled release system of the present invention.

DETAILED DESCRIPTION

The present invention features a method of controlling the release rate of a fragrance and other active ingredients, that can be incorporated in consumer and diversified products, and provide fragrance release over an extended period of time, or yields a high impact fragrance "burst" upon treating the target site with heat. The carrier system of the present invention comprises a free-flowing, powder formed of solid hydrophobic nano-spheres comprising fragrances, as well as other active ingredients, that are encapsulated in a pH or salt sensitive micro-sphere, as shown in FIG. 1. The composition is activated by changes in pH or salt concentration in the system proximate environment, to provide prolonged release of fragrances and other active ingredients over an extended period of time, or yield a high impact fragrance "burst" upon treating the target surface with heat, such as blow drying the hair or ironing the fabric.

The term "spheres" is intended to describe solid, substantially spherical particulates. It will be appreciated that the term "sphere" includes other particle shapes that can be formed in accordance with the teachings of the present invention.

The term "pH or salt triggered release" is intended to mean that the rate of release is dependent of or regulated by the pH or by salt concentration of the system surrounding media or environment.

In one embodiment, the nano-spheres of the present invention can have high cationic charge density. High cationic charge density on the nano-sphere surface can be created by incorporating a cationic surface active agents into the solid hydrophobic matrix of the nano-spheres, by incorporating a cationic charge "booster" in the pH or salt sensitive micro-sphere matrix, or by using a cationic surface active agent in the nano-sphere matrix in conjunction with a cationic charge "booster" in the micro-sphere matrix.

Fragrance containing nano-spheres of the present invention have an average diameter in the range from about 0.01 micron to about 10 microns. Preferably, the sphere size of the fragrance-containing nano-spheres is in the range from about 0.05 microns to about 2 microns. It has been found that spheres within the range of about 0.5 microns to about 1 micron are efficiently entrained on fabric surfaces and are not noticeable on the fabrics. This linear dimension for any individual sphere represents the length of the longest straight line joining two points on the surface of the sphere.

Fabric care components can be added to the carrier system or can be incorporated into the nano-sphere matrix, the micro-spheres matrix, or both the nano and micro spheres matrices. Suitable fabric care components include: ironing aids such as silicones; anti-shrinkage agents; anti-wrinkle agents; fabric crisping agents; fabric softening agents, spotting agents; bleaching agents, germicides; fungicides; stabilizers preservatives; bactericides which can be effective to protect the composition or to treat fabrics; flow agents; other active ingredients, and mixtures thereof.

Additional components can be added to the fragrance carrier system or can be incorporated into the nano-spheres, the micro-spheres, or both the nano and micro spheres matrices. The controlled release system of the present invention can readily include other cosmetic, dermatological, and pharmaceutical active agents, including, but are not limited to: anti-oxidants; free radical scavengers; moisturizers; depigmentation agents; reflectants; humectants; ant microbial agents; antibacterial agents; allergy inhibitors; anti-acne agents; anti-aging agents; anti-wrinkling agents, antiseptics; analgesics; anti-hair loss agents; hair growth promoting agents; hair growth inhibitor agents,; keratolytic agents; anti-inflammatory agents; fresheners; healing agents; anti invectives; inflammation inhibitors; vasoconstrictors; vasodilators; wound healing promoters; peptides, polypeptides and proteins; deodorants and antiperspirants; skin emollients and skin moisturizers; hair conditioners; hair softeners; hair moisturizers; tanning agents; skin lightening agents; anti-fungal; depilating agents; counterirritants; poison ivy products; poison oak products; burn products; make-up preparations; vitamins; amino acids and their derivatives; herbal extracts; flavoids; skin conditioners; chelating agents; cell turnover enhancers; coloring agents; sunscreens; nourishing agents; moisture absorbers; sebum absorbers and the like; skin penetration enhancers; other active ingredients, and mixtures thereof. The additional components are usually present in an amount from about 1% to about 20% by weight of the spheres.

I. Matrix Materials for Forming the Nano-Spheres

I a. Hydrophobic Materials

Suitable solid core materials for forming nano-spheres of the present invention are inert nontoxic hydrophobic materials with a melting point range between about 30 degrees C. and about 90 degrees C. Examples of hydrophobic materials include natural, regenerated, or synthetic waxes including animal waxes such as beeswax, lanolin and shellac wax, vegetable waxes such as carnauba, candelilla, sugar cane, rice bran, and bayberry wax, mineral waxes such as petroleum waxes including paraffin and microcrystalline wax, and mixtures thereof. Other hydrophobic materials which can be used in the present invention include wax and silicon copolymers, such as candelilla wax and silicone copolymer, ozokrite wax and silicon copolymers, beeswax and silicon copolymers, and the like. Other hydrophobic compounds which can be used in the present invention include: fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol, solid hydrogenated castor and vegetable oils, hard paraffins, hard fats, and mixtures thereof. Other hydrophobic compounds which can be used, include triglycerides, preferably of at least food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10–18), denoted medium chain triglycerides (MCT). The fatty acid moieties of such triglycerides can be unsaturated or polyunsaturated and mixtures of triglycerides having various fatty acid material. The nano-sphere matrix can comprise a single hydrophobic material or a mixture of a plurality of materials. Other hydrophobic materials that are known to those skilled in the art and suitable materials as described in "Industrial Waxes" Vol. I and II, by Bennett F. A. I. C., published by Chemical Publishing Company Inc., 1975 and Martindale, "The Extra Pharmacopoeia", The Pharmaceutical Press, $28^{th}$ Edition pp. 1063–1072, 1982 can be used in the present invention.

Other hydrophobic compounds which can be used in the present invention include synthetic polymers, such as alkylated polyvinylpyrrolidines, the Ganex® copolymer series, and ProLipid® 151, commercially available from the ISP Company. Examples of other suitable hydrophobic polymers and copolymer for use as the matrix material include silicon waxes commercially available from Lambent Technologies of Norcross, Ga., and polyethylene homopolymers A-C® 1702; A-C® 617, A-C® 617A, and A-C® 15, commercially available from Allied Signal Inc.; PERFORMALENE™ PL available from Baker Pertolite Co.; polyethylene homopolymer commercially available from New Phase Technologies; ETHYLENE-ACRYLIC ACID COPOLYMERS A-C® 540, A-C® 540A, and A-C® 580 commercially available from Allied Signal Inc.; polyamides having a molecular weight in the range of from about 6,000 up to about 12,000, for example, MACROMELT™ 6030 manufactured by the Henkel Ag. of Dusseldorf, Germany; VERSALON™ 1135 polyamide polymer available commercially from General Mills, Inc.

I b. Cationic Surface Active Agents

The nano-spheres of the present invention can comprise any of the cationic surface active agents known in the art. Hydrocarbon conditioners suitable for use herein are selected from the following classes of compounds:

(i) Cationic quaternary ammonium salts. Examples of cationic quaternary ammonium salts include, but are not limited to:

(1) Acyclic quaternary ammonium salts having at least two $C_{8-30}$, preferably $C_{12-22}$ alkyl chains, such as: ditallowdimethyl ammonium methylsulfate, di(hydrogenated tallow) dimethyl ammonium methylsulfate, distearyldimethyl ammonium methylsulfate, dicocodimethyl ammonium methylsulfate and the like;

(2) Cyclic quaternary ammonium salts of the imidazolinium type such as di(hydrogenated tallow)dimethyl imidazolinium methylsulfate, 1-ethylene-bis(2-tallow-1-methyl) imidazolinium methylsulfate and the like;

(3) Diamido quaternary ammonium salts such as: methyl-bis(hydrogenated tallow amidoethyl)-2-hydroxyethyl ammonium methyl sulfate, methyl bis(tallowamidoethyl)-2-hydroxypropyl ammonium methylsulfate and the like;

(4) Biodegradable quaternary ammonium salts such as N,N-di (tallowoyl-oxy-ethyl)-N,N,-dimethyl ammonium methyl sulfate and N,N-di (tallowoyl-oxy-propyl)-N,N-dimethyl ammonium methyl sulfate. Biodegradable quaternary ammonium salts are described, for example, in U.S. Pat. Nos. 4,137,180, 4,767,547 and 4,789,491 incorporated herein by reference into this application.

Preferred biodegradable quaternary ammonium salts include the biodegradable cationic diester compounds, as described in U.S. Pat. No. 4,137,180, incorporated herein by reference into this application.

(ii) Tertiary fatty amines having at least one and preferably two $C_8$ to $C_{30}$, preferably $C_{12}$ to $C_{22}$ alkyl chains. Examples include hardened tallow-di-methylamine and cyclic amines such as 1-(hydrogenated tallow)amidoethyl-2-(hydrogenated tallow)imidazoline. Cyclic amines which may be employed for the compositions herein are described in U.S. Pat. No. 4,806,255 incorporated herein by reference into this application.

(iii) Carboxylic acids having 8 to 30 carbons atoms and one carboxylic group per molecule. The alkyl portion has 8 to 30, preferably 12 to 22 carbon atoms. The alkyl portion may be linear or branched, saturated or unsaturated, with linear saturated alkyl preferred. Stearic acid is a preferred fatty acid for use in the composition herein. Examples of these carboxylic acids are commercial grades of stearic acid and palmitic acid, and mixtures thereof which may contain small amounts of other acids.

(iv) Esters of polyhydric alcohols such as sorbitan esters or glycerol stearate. Sorbitan esters are the condensation products of sorbitol or iso-sorbitol with fatty acids such as stearic acid. Preferred sorbitan esters are monoalkyl. A common example of sorbitan ester is SPAN 60 (ICI) which is a mixture of sorbitan and isosorbide stearates.

(v) Fatty alcohols, ethoxylated fatty alcohols, alkylphenols, ethoxylated alkylphenols, ethoxylated fatty amines, ethoxylated monoglycerides and ethoxylated diglycerides.

(vi) Mineral oils, and polyols such as polyethylene glycol.

(vii) Silicone oils and silicone surfactants as described in U.S. Pat. No. 5,174,911 and U.S. application Ser. No. 07/776,719, now U.S. Pat. No. 5,300,238 incorporated herein by reference into this application.

These softeners are more definitively described in U.S. Pat. No. 4,134,838 the disclosure of which is incorporated by reference herein.

Other quaternary ammonium salt fabric conditioning compounds suitable for use are disclosed by Morton D. R. et al. in U.S. Pat. No. 3,686,025 and 6,083,899 are described in "Cationic Surfactants", Surfactant Science series, Vol. 34, edited by Richmond J. M., Marcel Dekker Inc., 1990, which are incorporated herein by reference into this application.

The particularly preferred cationic fabric conditioning agents for the fragrance carrier of the present invention are: behenyltrimethylammonium chloride; ditallowdimethylammonium methylsulfate; ditallowdimethylammonium chloride; methyl(1) stearylamidoethyl (2) stearylimidazolinium methosulfate; methyl(1)stearylamidoethyl(2)stearylimidazolinium chloride; N,N-di(tallowyl-oxy-ethyl)-N,N-dimethyl ammonium chloride; N,N-di(canolyl-oxy-ethyl)-N,N-dimethyl ammonium chloride; N,N-di(tallowyl-oxy-ethyl)-N-methyl, N-(2-hydroxyethyl) ammonium chloride; N,N-di (canolyl-oxy-ethyl)-N-methyl, N-(2-hydroxyethyl) ammonium chloride; N,N-di(2-tallowyloxy-2-oxo-ethyl)-N, N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowoyloxy-2-ethyl)-N-(2-tallowyloxy-2-oxo-ethyl)-N,N-dimethyl ammonium chloride; N-(2-canolyloxy-2-ethyl)-N-(2-canolyloxy-2-oxo-ethyl)-N,N-dimethyl ammonium chloride; N,N,N-tri(tallowyl-oxy-ethyl)-N-methyl ammonium chloride; N,N,N-tricanolyl-oxy-ethyl)-N-methyl ammonium chloride; N-(2-tallowyloxy-2-oxoethyl)-N-(tallowyl)-N,N-dimethyl ammonium chloride; N-(2-canolyloxy-2-oxoethyl)-N-(canolyl)-N,N-dimethyl ammonium chloride; 1,2-ditallowyloxy-3-N,N,N-trimethylammoniopropane chloride; and 1,2-dicanolyloxy-3-N,N,N-trimethylammoniopropane chloride; and mixtures of thereof.

Methyl-1-tallowamidoethyl-2-tallowimidazolinium methylsulfate available from Witco Chemical Company under the name Varisoft™ 475. Examples of monoalkyltrimethylammonium salts are monotallowtrimethylammonium chloride, mono(hydrogenated tallow)trimethylammonium chloride, palmityltrimethyl ammonium chloride and soyatrimethylammonium chloride, available from Witco Chemical Company under the names Adogen™ 471, Adogen™ 441, Adogen™ 444, and Adogen™ 415, respectively. Examples of behenyltrimethylammonium chloride are commercially available under the name Kemamine™ Q2803-C from Humko Chemical Division of Witco Chemical Corporation. Methylbis(tallowamidoethyl)(2-hydroxyethyl)ammonium methylsulfate and methylbis(hydrogenated tallowamidoethyl)(2-hydroxyethyl)ammonium methylsulfate; are available from Witco Chemical Company under the names Varisoft™ 222 and Varisoft™ 110, respectively: dimethylstearylbenzyl ammonium chloride sold under the names Varisoft™ SDC by Witco Chemical Company and Ammonyx™ 490 by Onyx Chemical Company.

The most preferred quaternary ammonium salt fabric conditioning agents are methyl bis(hydrogenated ditallowamidoethyl) 2 hydroxyethyl ammonium chloride, commercially available from Croda Inc. under the name INCROSOFT® 100; methyl bis(hydrogenated tallow amidoethyl)-2-hydroxyethyl ammonium methyl sulfate, commercially available from the Stepan Company under the name ACCOSOFT® 440-75 DEG; methyl (1) hydrogenated tallow amidoethyl-(2) hydrogenated tallow imidazolinium methyl sulfate, commercially available from the Stepan Company under the name ACCOSOFT® 808 HT; behenyltrimethylammonium chloride, commercially available under the trade name Kemamine™ Q2803-C from Humko Chemical Division of Witco Chemical Corporation. The cationic surface-active agents for hair and skin care applications are cetyl trimethylammonium chloride and behenamidopropyl hydroxyethyl dimonium chloride Hydrophobic cationic conditioning agents can also be included in the nano-sphere matrix, including fabric conditioning agents, hair conditioning agents, and skin conditioning agents. The nano-spheres matrix can comprise of 100% of these conditioning agents, by weight.

It is preferred that the nano-spheres of the present invention have a melting point in the range from about 30 degrees C. to about 90 degrees C., preferably from about 40 degrees C. to about 90 degrees C. The melting point of the spheres is usually a function of the carrier matrix employed. Accordingly, preferred matrix materials have a melting point in the range of about 50 degrees C. to about 80 degrees C., preferably from about 60 degrees C. to about 70 degrees C. It should be understood that it is the melting point of the sphere rather than of the carrier matrix that is important for use of the carrier system of the present invention.

Considerations in the selection of the matrix material include good barrier properties to the active agents and the fragrance ingredients, low toxicity and irritancy, stability, and high loading capacity for the active agents of interest.

II. Materials for Forming a Micro-Sphere Matrix

IIa. pH and Salt Sensitive Materials

Any material and structural form may be used as the pH-sensitive or salt-sensitive trigger means that maintains the integrity of the micro-sphere until triggered by a solution of the desired pH. Typically, the trigger pH is between about 3 to 12, although in some applications it may be higher or lower. Preferably, the trigger pH is from about 7 to about 9 for fabric, hair and skin applications. The trigger pH is the threshold pH value or range of values at which either above or below the trigger pH the pH-sensitive material degrades, and/or dissolves. The micro-sphere can be formed to be stable in solutions and then as the pH rises above the trigger pH the microspheres are activated. Likewise, micro-spheres can be formed to be stable in solutions and as the pH drops below the trigger pH the microspheres are activated. Once activated, the active ingredients and the nano-spheres are released.

In one embodiment a pH-sensitive trigger means is used that the micro-sphere is capable of becoming more permeable to water and/or losing physical strength following triggering by a solution of the desired pH, either above or below the trigger pH, or salt concentration.

In another embodiment a pH-sensitive trigger means is used to hold together two nano-sphere portions. The trigger means is capable of losing its adhesive quality or strength, such as to degrade or dissolve, following triggering by a solution of the desired pH, either above or below the trigger pH, or following a change in salt concentration. The reduction in adhesion strength allows the hydrostatic pressure inside the micro-sphere core to push apart the nano-spheres portions held together by the adhesive trigger means, thus releasing the contents.

The pH-sensitive materials can be insoluble solids in acidic or basic aqueous solutions, which dissolve, or degrade and dissolve, as the pH of the solution is neutral. The pH-sensitive materials can be insoluble solids in acidic or basic aqueous solutions which dissolve, or degrade and dissolve, as the pH of the solution rises above or drops below a trigger pH value.

Exemplary pH-sensitive materials include copolymers of acrylate polymers with amino substituents, acrylic acid esters, polyacrylamides, phthalate derivatives (i.e., compounds with covalently attached phthalate moieties) such as acid phthalates of carbohydrates, amylose acetate phthalate, cellulose acetate phthalate, other cellulose ester phthalates, cellulose ether phthalates, hydroxy propyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymers, formalized gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives such as acrylic acid and acrylic ester copolymers, methacrylic acid and esters thereof, vinyl acetate and crotonic acid copolymers.

Examples of suitable pH sensitive polymers for use are the Eudragit® polymers series from Rohm America Inc., a wholly-owned subsidiary of Degussa-Huls Corporation, headquartered in Piscataway, N.J., and an affiliate of Rohm GmbH of Darmstadt, Germany. EUDRAGIT® L 30 D-55 and EUDRAGIT® L 100-55, pH dependent anionic polymer that is soluble at pH above 5.5 and insoluble blow pH 5. These polymers can be utilized for targeted drug delivery in the duodenum. EUDRAGIT® L 100 pH dependent anionic polymer that is soluble at pH above 6.0 for targeted drug delivery in the jejunum. EUDRAGIT® S 100 pH dependent anionic polymer that is soluble at pH above 7.0 for targeted drug delivery in the ileum. EUDRAGIT® E 100 and EUDRAGIT® EPO, pH dependent cationic polymer, soluble up to pH 5.0 and insoluble above pH 5.0.

Other pH-sensitive materials are cationic pH sensitive polymers and copolymers that are water insoluble at pH 9 and above and are water soluble or water dispersible at pH 7.

Additional pH-sensitive materials include poly functional polymers containing multiple groups that become ionized as the pH drops below their pKa. A sufficient quantity of these ionizable groups must be incorporated in the polymer such that in aqueous solutions having a pH below the pKa of the ionizable groups, the polymer dissolves. These ionizable groups can be incorporated into polymers as block copolymers, or can be pendent groups attached to a polymer backbone, or can be a portion of a material used to crosslink or connect polymer chains. Examples of such ionizable groups include polyphosphene, vinyl pyridine, vinyl aniline, polylysine, polyornithine, other proteins, and polymers with substituents containing amino moieties.

The pH-sensitive and salt sensitive materials can be blended with an inert water sensitive material. By inert is meant a material that is not substantially affected by a change in pH or salt concentration in the triggering range. By altering the proportion of a pH-sensitive material to inert material the time lag subsequent to triggering and prior to release can be tailored.

IIb. Water Sensitive Materials

Water-sensitive materials that can be mixed with the pH or salt sensitive materials to form the micro-spheres of the present invention comprises of polyvinyl pyrrolidone, water soluble celluloses, polyvinyl alcohol, ethylene maleic anhydride copolymer, methyl vinyl ether maleic anhydride copolymer, polyethylene oxides, water soluble polyamide or polyester, copolymers or homopolymers of acrylic acid such as polyacrylic acid, polystyrene acrylic acid copolymers or starch derivatives, polyvinyl alcohol, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

The polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I–XIV of U.S. Pat. No. 5,051,222 issued on Sep. 24, 1991, the specification for which is incorporated by reference herein.

Polyvinyl alcohol useful for practice of the present invention is Mowiol® 3–83, having a molecular weight of about 14,000 Da and degree of hydrolysis of about 83%, Mowiol® 3–98 and a fully hydrolyzed (98%) polyvinyl alcohol having a molecular weight of 16,000 Da commercially available from Gehring-Montgomery, Inc. of Warminister Pa. Other suitable polyvinyl alcohols are: AIRVOL® 205, having a molecular weight of about 15,000–27,000 Da and degree of hydrolysis of about 88%, and VINEX® 1025, having molecular weight of 15,000–27,000 Da degree of hydrolysis of about 99% and commercially available from Air Products & Chemicals, Inc. of Allentown, Pa.; ELVANOL® 51 -05, having a molecular weight of about 22,000–26,000 Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; and GOHSENOL® GL-03 and GOHSENOL® KA-20 commercially available from Nippon Gohsei K.K., The Nippon Synthetic Chemical Industry Co., Ltd., of No. 9-6, Nozaki Cho,Kita-Ku, Osaka, 530 Japan.

Suitable polysaccharides are polysaccharides of the non-sweet, coloidally-soluble types, such as natural gums, for example, gum arabic, starch derivates, dextrinized and hydrolyzed starches, and the like. A suitable polysaccharide is a water dispersible, modified starch commercially available as Capule®, N-Lok®, Hi-Cap™ 100 or Hi-Cap™ 200 commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

IIc. Cationic Charge Boosters

The carrier system of the present invention can comprise a cationic charge booster to enhance the cationic charge density on the nano-sphere surface. Suitable cationic charge boosters are described in U.S. Pat. No. 6,083,899 hereby incorporated by reference into this application. The preferred cationic charge boosters of the present invention are described herein below.

Quaternary Ammonium Compounds

A preferred composition of the present invention comprises at least about 0.1%, preferably from about 0.1% to about 10%, more preferably from about 0.1% to about 5% by weight, of a cationic charge booster having the formula:

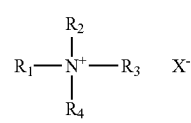

wherein $R_1$, $R_2$, $R_3$, and $R_4$ are each independently $C_1$–$C_{22}$ alkyl, $C_3$–$C_{22}$ alkenyl, $R_5$—Q—$(CH_2)_m$—, wherein $R_5$ is $C_1$–$C_{22}$ alkyl, and mixtures thereof, m is from 1 to about 6; X is an anion. Preferably $R_1$ is $C_6$–$C_{22}$ alkyl, $C_6$–$C_{22}$ alkenyl, and mixtures thereof, more preferably $R_1$ $C_{11}$–$C_{18}$ alkyl, $C_{11}$–$C_{18}$ alkenyl, and mixtures thereof, $R_2$, $R_3$, and $R_4$ are each prefer $C_1$–$C_4$ alkyl, more preferably each $R_2$, $R_3$, and $R_4$ are methyl.

Alternatively, $R_1$ can be a $R_5$ —Q—$(CH_2)_m$— moiety wherein $R_5$ is an alkyl or alkenyl moiety having from 1 to 22 carbon atoms, preferably the alkyl or alkenyl moiety when taken together with the Q unit is an acyl unit. For example Q can be derived from a source of triglyceride selected from tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

An example of a fabric softener cationic booster comprising a $R_5$ —Q—$(CH_2)_m$— moiety has the formula:

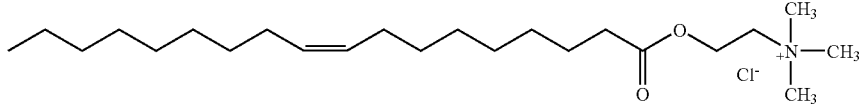

wherein $R_5$ —Q— represents oleoyl units and m is equal to 2.

Preferably X is a softener compatible anion, such as the anion of a strong acid. For example, X can be chloride, bromide, methylsulfate, ethylsulfate, sulfate, nitrate and mixtures thereof. More preferably X is chloride and methyl sulfate.

Polyvinyl Amines

A preferred composition according to the present invention contains at least about 0.1%, preferably from about 0.1% to about 10%, more preferably from about 0.1% to about 5% by weight, of one or more polyvinyl amines charge boosters having the formula

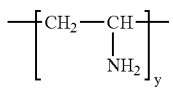

wherein y is from about 3 to about 10,000, preferably from about 10 to about 5,000, more preferably from about 20 to about 500. Polyvinyl amines suitable for use in the present invention are available from BASF under the name Lupasol® LU 321. The greater number of amine moieties per unit weight on the polyvinyl amines provides preferred substantial charge density.

Polyalkyleneimines

A preferred composition of the present invention comprises at least about 0.1%, preferably from about 0.1% to about 10%, more preferably from about 0.1% to about 5% by weight, of a polyalkyleneimine charge booster having the formula:

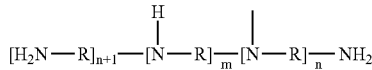

wherein the value of m is from 2 to about 700 and the value of n is from 0 to about 350. Preferably the compounds of the present invention comprise polyamines having a ratio of m:n that is at least 1:1 but may include linear polymers (n equal to 0) as well as a range as high as 10:1, preferably the ratio is 2:1. When the ratio of m:n is 2:1, the ratio of primary:secondary:tertary amine moieties of —$RNH_2$, —RNH, and —RN moieties, is 1:2:1. R can be $C_2$–$C_8$ alkylene, $C_3$–$C_8$ alkyl substituted alkylene, and mixtures thereof. Preferably R is ethylene, 1,2-propylene, 1,3-propylene, and mixtures thereof, and more preferably ethylene. R radicals serve to connect the amine nitrogens of the backbone.

Optionally, one or more of the polyvinyl amine backbone —$NH_2$ unit hydrogens can be substituted by an alkyleneoxy unit having the formula:

wherein $R_1$ is $C_2$–$C_4$ alkylene; $R_2$ is hydrogen, $C_1$–$C_4$ alkyl, and mixtures thereof; and x is from 1 to 50. In one embodiment or the present invention the polyvinyl amine is reacted first with a substrate which places a 2-propyleneoxy unit directly on the nitrogen followed by reaction of one or more moles of ethylene oxide to form a unit having the general formula:

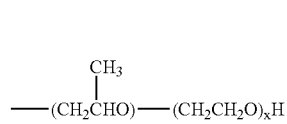

wherein x has the value of from 1 to about 50. Substitutions such as the above are represented by the abbreviated formula PO—$EO_X$—. However, more than one propyleneoxy unit can be incorporated into the alkyleneoxy substituent.

The preferred polyamine cationic charge boosters of the present invention comprise backbones wherein less than about 50% of the R groups comprise more than 3 carbon atoms. The use of two and three carbon spacers as R moieties between nitrogen atoms in the backbone is advantageous for controlling the charge booster properties of the molecules. More preferred embodiments of the present invention comprise less than about 25% moieties having more than 3 carbon atoms. Yet more preferred backbones comprise less than about 10% moieties having more than 3 carbon atoms. Most preferred backbones comprise about 100% ethylene moieties.

The cationic charge boosting polyamines of the present invention comprise homogeneous or non-homogeneous polyamine backbones, preferably homogeneous backbones. For the purpose of the present invention the term "homogeneous polyamine backbone" is defined as a polyamine backbone having R units that are the same such as, all ethylene. However, this definition does not exclude polyamines that comprise other extraneous units comprising the polymer backbone that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of one or more alkylene or substituted alkylene moieties, for example, ethylene and 1,2-propylene units taken together as R units.

However, not all of the suitable charge booster agents belonging to this category of polyamine comprise the above described polyamines. Other polyamines that comprise the backbone of the compounds of the present invention are generally polyalkyleneamines (PAA's), polyalkyleneimines (PAI's), preferably polyethyleneamine (PEA's), or polyethyleneimines (PEI's). Polyethyleneimines suitable for use in the present invention are available from BASF under the trade name Lupasol® such as Lupasol™ PR8515, having an average molecular weight of 1,800. A common polyalkyleneamine (PAA) is tetrabutylenepentamine. PEA's can be obtained by reactions involving ammonia and ethylene dichloride, followed by fractional distillation. The common PEA's obtained are triethylenetetramine (TETA) and tetraethylenepentamine (TEPA). Above the pentamines, such as, the hexamines, heptamines, octamines and possibly non-amines, the cogenerically derived mixture does not appear to separate by distillation and can include other materials such as cyclic amines and particularly piperazines.

Poly-Quaternary Ammonium Compounds

A preferred composition of the present invention comprises at least about 0.1%, preferably from about 0.1% to about 10%, more preferably from about 0.1% to about 5% by weight, of a cationic charge booster having the formula:

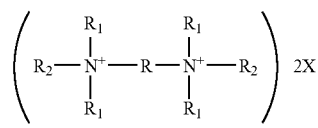

wherein R is substituted or unsubstituted $C_2$–$C_{12}$ alkylene, substituted or unsubstituted $C_2$–$C_{12}$ hydroxyalkylene; each $R_1$ is independently $C_1$–$C_4$ alkyl, each $R_2$ is independently $C_1$–$C_{22}$ alkyl, $C_3$–$C_{22}$ alkenyl, $R_5$ —Q—$(CH_2)_m$—, wherein $R_5$ is $C_1$–$C_{22}$ alkyl, $C_3$–$C_{22}$ alkenyl, and mixtures thereof; m is from 1 to about 6; Q is a carbonyl unit as described above and mixtures thereof; X is an anion.

Preferably R is ethylene and $R_1$ is preferably methyl or ethyl, more preferably methyl. Preferably at least one $R_2$ is $C_1$–$C_4$ alkyl, more preferably methyl. Most preferably at least one $R_2$ is $C_{11}$–$C_{22}$ alkyl, $C_{11}$–$C_{22}$ alkenyl, and mixtures thereof.

Alternatively $R_2$ is a $R_5$ —Q—$(CH_2)_m$— moiety wherein $R_5$ is an alkyl moiety having from 1 to 22 carbon atoms, preferably the alkyl moiety when taken together with the Q unit is an acyl unit derived from a source of triglyceride selected from the group consisting of tallow, partially hydrogenated tallow, lard, partially hydrogenated lard, vegetable oils, partially hydrogenated vegetable oils, such as, canola oil, safflower oil, peanut oil, sunflower oil, corn oil, soybean oil, tall oil, rice bran oil, and the like and mixtures thereof.

An example of a fabric softener cationic booster comprising a $R_5$ —Q—$(CH_2)_m$— moiety has the formula:

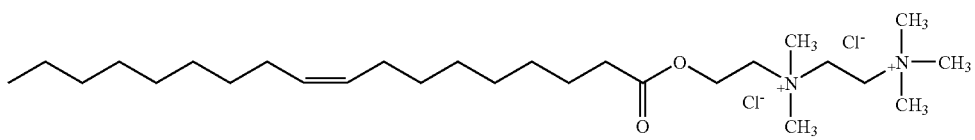

wherein $R_1$ is methyl, one of the $R_2$ units is methyl and the other of the $R_2$ unit is $R_5$ —Q—$(CH_2)_m$— wherein $R_5$ —Q— is an oleoyl unit and m is equal to 2. X is a softener compatible anion, such as an anion of a strong acid. For example, X can be chloride, bromide, methylsulfate, ethylsulfate, sulfate, nitrate and mixtures thereof. More preferably chloride and methyl sulfate.

Active Ingredients

Fragrances

A fragrance can be included in the carrier system of the present invention. The fragrance that can be encapsulated in the carrier system of the present invention can be any odoriferous material and can be selected according to the desires of the fragrance creator. In general terms, such fragrance materials are characterized by a vapor pressure below atmospheric pressure at ambient temperatures. The high boiling perfume materials employed herein will most often be solids at ambient temperatures, but also can include high boiling liquids. A wide variety of chemicals are known for perfumery uses, including materials such as aldehydes, ketones, esters, and the like. More commonly, naturally occurring plant and animal oils and exudates comprising complex mixtures of various chemical components are known for use as fragrances, and such materials can be used herein. Fragrances useful for the present invention can be a single aroma chemical, relatively simple in their composition, or can comprise highly sophisticated, complex mixtures of natural and synthetic chemical components, all chosen to provide any desired odor.

Suitable fragrance which can be used in the present invention comprise, for example the high boiling components of woody/earthy bases containing exotic materials such as sandalwood oil, civet, patchouli oil, and the like. The perfumes herein can be of a light, floral fragrance, such as for example, high boiling components of rose extract, violet extract, and the like. The perfumes herein can be formulated to provide desirable fruity odors, such as for example lime, lemon, orange, and the like. The perfume can be any material of appropriate chemical and physical properties which exudes a pleasant or otherwise desirable odor when applied to fabrics. Perfume materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

Vitamins

Various vitamins can be included in the release system of the present invention. For example, vitamin A and derivatives thereof, vitamin $B_2$, biotin, pantothenic acid, vitamin K, vitamin D, vitamin E and mixtures thereof can be used.

Sunscreens

The sunscreen agents that can be incorporated into the aqueous composition. The term "sunscreen agent" as used herein defines ultraviolet ray-blocking compounds exhibiting absorption within the wavelength region between about 290 and about 400 nm. Sunscreens can be classified into five groups based upon their chemical structure: para-amino benzoates; salicylates; cinnamates; benzophenones; and miscellaneous chemicals including menthyl anthranilate and digalloyl trioleate. Inorganic sunscreens can also be used including titanium dioxide, zinc oxide, iron oxide and polymer particles such as those of polyethylene, polymethylmethacrylates and polyamides. Preferred materials include: p-aminobenzoic acid and its derivatives; anthranilates; salicylates; cinnamates; coumarin derivatives; azoles; tannic acid; and its derivatives.

A wide variety of conventional sunscreening agents are suitable for use in the present invention as described in Segarin et al., at Chapter VIII, Pages 189 et seq., "Cosmetics Science and Technology", the disclosure of which is incorporated herein by reference. Specific suitable sunscreening agents include, for example:

p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxynaphthoic acid and its salts, o- and p-hydroxy-biphenyldisulfonates, coumarin derivatives, diazoles quinine salts, quinoline derivatives, hydroxy or methoxy substituted benzophenones, uric and vilouric acids, tannic acid and its derivatives, hydroquinone, benzophenones, and the like.

Anti-Inflammatory Agents

Anti-inflammatory can be included in the controlled release system of the present invention to enhance photo protection benefits, particularly from UVA. Suitable steroidal antiinflamatories include hydrocortisone; non-steroidal antiinflamatories such as oxicans, salicylates, acetic acid derivatives, fenamates, propionic acid derivatives, pyrazoles, substituted phenyl compounds, 2-naphthyl containing compounds, and natural antiinflamatories such as aloe vera. Examples of anti inflammatory are described in U.S. Pat. No. 5,487,884, the entire contents of which are incorporated herein by reference in this application.

Antioxidants

In addition to the fragrances, the controlled release system of the invention can also contain other antioxidants including those well known in the art. Representative antioxidants include vitamin E, tocopheryl acetate, betaglucan, coenzyme Q10, representative formula $CH_3C_6(O)_2(OCH_3)_2)CH_2CH$:$C(CH_3)CH_2!_nH$, butylated hydroxy toluene (BHT), butylat hydroxy anisole BHA, superoxide dismutose, propylgallate, and the like.

Skin Conditioners

In addition to the fragrance, the controlled release system of the invention can also contain other skin conditioners, moisturizers and surfactants may be included as additives. Illustrative conditioners include mineral oil, petrolatum, vegetable oils (such as soybean or maleated soybean oil), dimethicone, dimethicone copolyol, cationic monomers and polymers (such as guar hydroxypropyl trimonium chloride and distearyl dimethyl ammonium chloride) as well as combinations thereof. Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose and mixtures thereof.

Drugs

Suitable drugs which can be administered in the controlled release system of the present invention include but are in no way limited to anti-bacterial agents such as thimerosal, chloramine, boric acid, phenol, iodoform, chlorhexidine and other oral antiseptics, beta-lactam antibiotics, for example cefoxitin, n-formamidoyl thienamycin and other thienamycin derivatives, tetracyclines, chloramphenicol, neomycin, gramicidin, kanamycin, amikacin, sismicin and tobramycin; anti-inflammatory steroids such as cortisone, hydrocortisone, beta-methasone, dexamethasone, fluocortolone, prednisolone, triamcinolone and the like; non-steroidal anti-inflammatory drugs including flurbiprofen, ibuprofen, indomethacin, piroxicam, naproxen, antipyrine, phenylbutazone and aspirin; plaque dissolving substances, for example lysozyme chloride or amylase; and local anaesthetics such as lidocaine, procaine, benzocaine, xylocaine and the like. The biologically active ingredient can also be one or more antibiotics, such as penicillin, polymyxin B, vancomycin, kanamycin, erythromycin, niddamycin, metronidazole, spiramycin and tetracycline.

Sensory Markers

Suitable sensory markers are cooling agents, such as menthol derivatives, and heating agents, such as capzasin. The release of the sensory markers can be used to convey to the consumer the product performance, provide long lasting perception, and signal that a new application of the product is needed.

Preservatives

Preservatives can be incorporated into the controlled release system of the present invention to protect against the growth of potentially harmful microorganisms. While microorganisms tend to grow in the aqueous phase, microorganisms can also reside in the anhydrous or oil phase. As such, preservatives which have solubility in both water and oil are preferably employed in the present compositions. Suitable preservatives for compositions of the present invention are alkyl esters of parahydroxybenzoic acid. Other preservatives, which can be used include hydantoin derivatives, propionate salts, and a variety of quaternary ammonium compounds.

Appropriate preservatives can be selected to satisfy the preservative challenge test and to provide product stability. Particularly preferred preservatives are methylparaben, imidazolidinyl urea, sodium dehydroacetate, propylparaben, trisodium ethylenediamine tetraacetate (EDTA), and benzyl alcohol. The preservative can be selected based on the consideration of possible incompatibilities between the preservative and other ingredients in the release system. Preservatives are preferably employed in amounts ranging from about 0.01% to about 2% by weight of the composition.

Moisturizing Agents

Moisturizing agents, such as glycerol, sodium pyrrolidonecarboxylate, NMFs (normal moisturizing factors) and hyaluronic acid can be used in the release system of the present invention.

IV. Processing Method

IVa. Nano-Spheres

The encapsulated active agent in the nano-spheres of the present invention can be prepared by the steps of (1) heating hydrophobic materials to a temperature above the melting point to form a melt, (2) dissolving or dispersing the active agent in the melt, (3) emulsifying the melt in the aqueous phase; and (4) cooling the dispersion to ambient temperature to form a fine suspension.

The fragrance or other active ingredients can be incorporated into the hydrophobic solid nano-spheres. Preferably, about 1% to about 80% of and more preferably about 1% to about 60% by weight of the active agent is used in forming the nano-spheres.

IVb. Micro-Spheres

The controlled release system of the present invention can be prepared by the steps of (a) incorporating the selected fragrance, and other active agents into the hydrophobic interior of the nano-spheres, (b) forming an aqueous mixture comprising one or more active agents, the nano-spheres, and a pH or salt sensitive material, and (c) spray drying the mixture of the present invention to form a dry powder composition. Accordingly, the nano-spheres can be encapsulated into the micro-sphere structure. One or more of the active agents which can be the same or different than the active agents incorporated in the nano-sphere can be incorporated into the micro-sphere structure.

The invention also provides a fabric care product comprising the composition of the present invention such as fabric softener, laundry detergents, rinse added products, and other fabric care products, comprising the fragrance controlled release system of the present invention. Fabric laundered with powder laundry detergent and liquid fabric softener comprising the particles of the present invention were observed to exhibit high level of fragrance (high odor intensity) in both the wet and the dry state and fragrance perception on the dry laundered fabric has been observed to be perceived over an extended period of time, i.e., two to three weeks.

A process for producing the multi component controlled release system includes the following steps:

(i) heating a hydrophobic material to a temperature above the melting point to form a melt;

(ii) dissolving or dispersing the selected fragrance and a first active agent into the melt;

(iii) dissolving or dispersing a second active agent, and the pH or salt sensitive materials, in the aqueous phase and heating it to above the melting temperature of the hydrophobic material;

(iv) mixing the hot melt with the aqueous phase to form a dispersion;

(v) high shear homogenization of the dispersion at a temperature above the melting temperature until a homogeneous fine dispersion is obtained having a sphere size of from about 1 microns to about 2 microns;

(vi) cooling the dispersion to ambient temperature; and (vii) spray drying the emulsified mixed suspension to form a dry powder composition.

Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high sear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, July 1971, pp 245–265; Barreto, "Spray Dried Perfumes for Specialties, Soap and Chemical Specialties", December 1966; Maleeny, Spray Dried Perfumes, Soap and San Chem, January 1958, pp. 135 et seq.; Flinn and Nack, "Advances in Microencapsulation Techniques", Batelle Technical Review, Vo. 16, No. 2, pp. 2–8 (1967); U.S. Pat. Nos. 5,525,367; and 5,417,153 which are incorporated herein as references.

In the preferred embodiment, the active agent is present at a level from about 0.01% to about 60%, preferably from about 1% to about 50% by weight of the micro-sphere. In the preferred embodiment, the nano-spheres are generally present in the pH or salt sensitive matrix at a level from about 1% to about 80%, preferably from about 1% to about 60% by weight of the matrix material with the balance being the active agents, the cationic surface active agent, the cationic charge booster, and the pH or salt sensitive materials. In the preferred embodiment, the pH or salt sensitive matrix is generally present at a level from about 1% to about 80%, preferably from about 1% to about 60% by weight of the matrix material with the balance being the active agents, the cationic surface active agent, the cationic charge booster, and the hydrophobic materials.

In one embodiment micro-spheres are formed by mixing nano-spheres incorporating a selected active agent with the pH or salt sensitive material and an inert water sensitive material such as polyvinyl alcohol, or compositions of polyvinyl alcohol and polysaccharides, under conditions sufficient to encapsulate the nano-spheres. Preferably mixing a selected active agent with the polyvinyl alcohol, or compositions of polyvinyl alcohol and polysaccharides, until the emulsion is formed and then spray drying the emulsion to thereby form an encapsulated nano-sphere. In the preferred embodiment, the pH or salt sensitive matrix is formed of a pH or salt sensitive material and polyvinyl alcohol material at a level from about 1% to about 50%, preferably from about 1% to about 30% by weight of the matrix material with the balance being the amount by weight of active agents and an optimal amount of polysaccharides. In an alternate embodiment, the polyvinyl alcohol is present in the matrix material in an amount of about 1% to about 20% and the weight of the polysaccharides are present in the amount of about 1% to about 20%. In the preferred embodiment, the active agent composition is generally present at a level from about 0.01% to about 20% preferably from about 1% to about 20% by weight of the encapsulated active agent with the balance being the polyvinyl alcohol or polyvinyl alcohol and polysaccharides. Optionally other conventional ingredients known in the art such as preservatives, surfactants, can be used in accordance with the teachings of the present invention. The multi-component spheres of the present invention preferably have size of from about 0.5 micron to about 300 microns, more preferably from about 1 micron to about 200 microns, most preferably from about 2 microns to about 50 microns. The present invention preferably has minimal active agents on the surface of the spheres, preferably less than 1%.

Polyvinyl alcohol is an excellent barrier material to the permeation of the volatile fragrance ingredients, and as a result the controlled release systems of the present invention do not provide perceptible odor in the dry state. Upon wetting by a sufficient amount of aqueous fluid such as a body fluid, the matrix can either dissolve to provide a burst of the active ingredients, or swell and soften the matrix to slowly release the encapsulated active agents over an extended period of time, depending on the composition of the matrix, such as the ratio of polyvinyl alcohol to other matrix materials. The use of pH or salt activated microspheres which provide varying rates of diffusion are contemplated. For example, the active ingredients encapsulated in the pH or salt activated micro-spheres may diffuse at any of the rates of the following:

(i) at steady-state or zero-order release rate in which there is a substantially continuous release per unit of time;

(ii) a first-order release rate in which the rate of release declines towards zero with time; and (iii) a delayed release in which the initial rate is slow, but then increases with time.

It has been found that a greater amount of polyvinyl alcohol in the matrix provides slower release rate as compared to a matrix including a lesser amount of polyvinyl alcohol in combination with a polysaccharide.

Nano-spheres formed of a hydrophobic material provide a controlled release system in order to release the active agent over an extended period of time by molecular diffusion. Active agents in the hydrophobic matrix of the nano-spheres can be released by transient diffusion. The theoretical early and late time approximation of the release rate of the active ingredients dissolved in the hydrophobic matrix of the nano-spheres can be calculated from the following equations:

Early time approximation $(m_t/m_{sec}) < 0.4$ $$\frac{M_t}{M_\infty} = 4\left(\frac{D_p t}{\Pi r^2}\right)^{1/2} - \frac{D_p t}{r^2} \quad (1)$$

$$\frac{dM_t/M_\infty}{dt} = 2\left(\frac{D_p}{\Pi r^2 t}\right)^{1/2} - \frac{D_p}{r^2} \quad (2)$$

Late time approximation $(m_t/m_\infty) > 0.6$ $$\frac{M_t}{M_\infty} = 1 - \frac{4}{(2.405)^2} \exp\left(\frac{-(2.405)^2 D_p t}{r^2}\right) \quad (3)$$

$$\frac{dM_t/M_\infty}{dt} = 1 - \frac{4D_p}{r^2} \exp\left(\frac{-(2.405)^2 D_p t}{r^2}\right) \quad (4)$$

wherein:

r is the radius of the cylinder, m∞ is the amount fragrance released from the controlled release system after infinite time;

$m_t$ is the amount fragrance released from the controlled release system after time t; and $D_p$ is the diffusion coefficient of the fragrance or aroma chemical in the matrix.

The release rate for releasing the active agents from the hydrophobic nano-spheres is typically slower than the release rate for releasing active agent from the pH or salt sensitive matrix. The active agents can be selected to be incorporated into either the hydrophobic nano-spheres or the pH or salt sensitive matrix depending on the desired time for release of the active agents. For example, a predetermined first active agent can be incorporated in the pH or salt sensitive matrix to be released during the rinsing cycle and a predetermined second active agent can be incorporated in the hydrophobic nano-spheres for release over an extended period of time during or after the first agent has been released. For example, the pH or salt sensitive matrix formed in accordance with the present invention can release the first active agent at a predetermined pH or salt concentration to provide a "burst" with continued release of the first active agent and nano-spheres formed in accordance with the present invention can release the active agent depending on the release rate from an initial time such as within few days, up to a period of few weeks.

The carrier system of the present invention can be incorporated in fabric care products, hair care products and skin care products.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Preparation of a pH/Salt Sensitive Fragrance Delivery System

EXAMPLE 1

The fragrance used in the following examples is a fragrance composition that is not substantive on fabric when used as neat oil. The fragrance composition used is as follows:

| Perfume Composition | Component (% Wt.) |
|---|---|
| Geraniol | 30.0 |
| Dihydro Myrcenol | 25.0 |
| Linalool | 25.0 |
| Tetrahydro Linalyl Acetate | 20.0 |

The following procedure is used for the preparation of multi component controlled release system with a fragrance as the active agent in the hydrophobic nano-sphere matrix. The nano-sphere hydrophobic matrix is candelilla wax, commercially available from Strahl & Pitsch Inc. of West Babylon, N.Y., the cationic conditioning agent is methyl bis(hydrogenated ditallowamidoethyl) 2 hydroxyethyl ammonium chloride, commercially available from Croda Inc. as INCROSOFT 100, The micro-sphere cationic pH sensitive matrix is Eudragit® EPO (commercially available from Rohm America Inc. of Piscataway, N.J.), the water sensitive matrix is Hi-Cap™ 100 (commercially available from the National Starch and Chemical Company of Bridgewater, N.J.).

200 grams of candelilla wax is placed in an oven at 80 degrees ° C. and allowed to melt. 1500 grams of deionized water are placed into 1 gallon vessel, fitted with an all-purpose silicon rubber heater (Cole-Palmer Instrument Company). 300 grams of Eudragit® EPO (commercially available from Rohm America Inc. of Piscataway, N.J.) and 150 grams of Hi-Cap™ 100 (commercially available from the National Starch and Chemical Company of Bridgewater, N.J.) were added to the water and the aqueous solution is heated to 90 degree C. while mixing it with a propeller mixer. The candelilla wax is removed from the oven, 50 grams of the cationic fabric conditioning agent, methyl bis(hydrogenated ditallowamidoethyl) 2 hydroxyethyl ammonium chloride, commercially available from Croda Inc. as INCROSOFT 100, and 300 grams of the fragrance are mixed into the melt by hand with a glass rod. The fragrance/conditioning agent/wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 30% fragrance encapsulated in the solid hydrophobic nano-spheres. The multi component controlled release system obtained contains 30% fragrance, 20% candelilla wax, 5% conditioning agent, 30% pH sensitive material, and 15% water sensitive material.

EXAMPLE 2

The following procedure is used for the preparation of multi component controlled release system with a fragrance as the active agent in the hydrophobic nano-sphere matrix. The nano-sphere hydrophobic matrix is polyethylene homopolymer, commercially available from New Phase Technologies as PERFORMALENE™ PL, the cationic conditioning agent is Incroquat Behenyl HE, behenamidopropyl hydroxyethyl dimonium chloride (a fatty quaternary ammonium salt, commercially available from Croda) and LUPASOL™ PR815, a polyethyleneimine having an average molecular weight of 1800 (commercially available from BASF Corporation) was used as a cationic charge booster. The micro-sphere cationic pH sensitive matrix is Eudragit® EPO (commercially available from Rohm America Inc. of Piscataway, N.J.), the water sensitive matrix water sensitive matrix is Hi-Cap™ 100 (commercially available from the National Starch and Chemical Company of Bridgewater, N.J.).

200 grams of polyethylene homopolymer is placed in an oven at 90 degrees ° C. and allowed to melt. 1500 grams of deionized water are placed into 1 gallon vessel, fitted with an all-purpose silicon rubber heater (Cole-Palmer Instrument Company). 200 grams of Eudragit® EPO (commercially available from Rohm America Inc. of Piscataway, N.J.) and 249 grams of Hi-Cap™ 100 (commercially available from the National Starch and Chemical Company of Bridgewater, N.J.) and 1 gram of polyethyleneimine having an average molecular weight of 1800, commercially available from BASF Corporation as LUPASOL™ PR815 is added to the water and the aqueous solution is heated to 95 degree C. while mixing it with a propeller mixer. The polyethylene homopolymer is removed from the oven, 50 grams of the cationic hair conditioning agent, Incroquat Behenyl HE, behenamidopropyl hydroxyethyl dimonium chloride (a fatty quaternary ammonium salt, commercially available from Croda) and 300 grams of the fragrance are mixed into the polymer by hand with a glass rod. The fragrance/conditioning agent/polyethylene polymer mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 30% fragrance encapsulated in the solid hydrophobic nano-spheres. The multi component controlled release system obtained contains 20% hydrophobic polymer, 5% hair conditioning agent in hydrophobic matrix of the nano-spheres, 20% pH sensitive material, 24.9% water sensitive material, and 0.1% cationic charge "booster" in the water sensitive matrix of the microspheres.

Test Methods for Fabric Care Products

Twenty cotton towels having the following dimensions 14"×17" were used for evaluating the performance of the fragrance carrier spheres of the present invention. Ten of the towels were 100% cotton and ten were composed of a mixture of 65% polyester and 35% cotton. The fabric was laundered in an American washing machine Kenmore™ 90 series.

Wash Conditions:
Fabric Load: 20 towels
Laundry detergent sample size: 100 grams
Fabric softener sample size: 30 grams
Dosing into the machine: Laundry detergent was dosed directly into the machine
Fabric softener was placed in the dispenser
Water level: Small Load
Water temperature: Cold/Cold
Cycle: Short cycle
Water temperature: Cold/Cold
Rinse options: One rinse cycle
Speeds: Heavy duty The laundered fabric was line dried overnight in a fragrance free room. The dry fabric was folded into two and placed into an aluminum tray, approximately 5 cm deep, covered with a perforated aluminum sheet, in order to keep it out of view, up to the moment of the sniff-test. The sniff-test was performed on the dry laundered fabric in a "pre-ventilated" room by ten graders, 24 hours following wash. The laundered fabric was then covered with a perforated aluminum sheet, and was evaluated again after one week and two weeks by a sniff-test method.

Odor perception is, by its nature, a very subjective determination. According to the procedure, the samples to be tested are provided to a panel of ten odor specialists who independently rank odor intensity of the dry laundered fabric using a scale of 1 (no perceived odor) to 10 (high odor intensity). Samples yielding an odor ranking below about 2 possess an odor which would hardly be noticed by the general public.

Incorporation of the pH/Salt Sensitive Controlled Release System in Fabric Care Products

EXAMPLE 3

The performance of a powder laundry detergent product comprising the fragrance carrier system of Example 1 (i.e., the ability to increase fragrance deposition onto fabric, as well as the ability to prolong fragrance release from the dry laundered fabric over an extended period of time, or yield a high impact fragrance "burst" upon ironing the fabric) was evaluated and compared to the performance of the same detergent comprising the neat fragrance, at the same fragrance level. The unfragranced powder laundry detergent base was a commercial TIDE™ FREE powder laundry detergent available from Procter & Gamble Company of Cincinnati, Ohio that is fragrance free.

The laundry samples were prepared at a 1% effective fragrance concentration using the fragrance described in Example 1. The control sample was prepared by weighting into a jar 1 gram of the neat fragrance and 99 grams of the TIDE™ FREE unfragranced and the resulting mixture was mixed for about one hour. The powder laundry detergent comprising the fragrance spheres of the present invention was prepared by weighting into a jar 3.3 grams of the fragrance spheres of example 2 and 96.7 grams of the TIDE™ FREE unfragranced powder laundry detergent base and the resulting mixture was mixed for about one hour.

Twenty towels were placed in the washing machine (10 of the towels used were 100% cotton and the other 10 towels were 65% polyester and 35% cotton) with 100 grams of powder laundry detergent dosed directly into the washing machine.

The following washing machine cycle was used:
Fabric Load: 20 towels
Laundry detergent sample size: 100 grams
Dosing into the machine: Laundry detergent was dosed directly into the machine
Water level: Small Load
Water temperature: Cold/Cold
Cycle: Short cycle
Water temperature: Cold/Cold
Rinse options: One rinse cycle
Speeds: Heavy duty Cloth samples were line-dried for 24 hours and then evaluated at four stages: immediately after drying (24 hours following wash); upon ironing 24 hours following wash; at one week after drying; and at two weeks after drying. The dry fabric was folded into two and placed into an aluminum tray, approximately 5 cm deep, covered with a perforated aluminum sheet, between the evaluation stages, up to the moment of the sniff-test. The sniff-test was performed on the dry laundered fabric in a "pre-ventilated" room by ten graders, and test results are presented below:

| | 24 Hours Following Wash | |
|---|---|---|
| Sample | Dry Fabric | Upon Ironing |
| Neat Fragrance (Control) | 3 | 5 |
| Encapsulated Fragrance (Example 1) | 7 | 8 |

Test results indicate that the cloth samples washed with the encapsulated fragrance of Example 1 are significantly more intense than the control samples washed with the neat fragrance immediately after drying (24 hours following wash).

A significant increase in fragrance intensity was observed upon ironing the fabric laundered with the encapsulated fragrance spheres of Example 1. Although odor intensity of the fabric laundered with the neat fragrance (control) was observed to be directly more intense, upon ironing, no significant increase in odor intensity was observed. Only a slight increase in odor intensity was observed when ironing the fabric laundered with the neat fragrance (control).

| Sample | One Week | Two Weeks |
|---|---|---|
| Neat Fragrance (Control) | 2 | 1 |
| Encapsulated Fragrance (Example 1) | 6 | 5 |

At week one and week two the test results indicate that the cloth samples washed with the encapsulated fragrance of Example 1 are significantly more intense than the control samples washed with the neat fragrance (control). The products comprising the encapsulated fragrance show significant improvement over the performance of the neat fragrance in sustaining the volatile constituents of the fragrance and providing a prolong fragrance release from the dry laundered fabric over an extended period of time.

Incorporation of the pH/Salt Sensitive Controlled Release System in Hair Care Products The ability of the control release of Example 2 to extend the release of a fragrance was determined by evaluating the odor intensity retained on hair washed with a shampoo composition comprising the controlled release system of example 2.

The shampoo samples were prepared at a 1% effective fragrance concentration using the fragrance described in Example 1. The control sample was prepared by weighting into a jar 1 gram of the neat fragrance and 99 grams of unfragranced shampoo base (30% concentrated shampoo base #4, product of JEEN International Corporation, of Little Fall, N.J. and 70% water) and the resulting mixture was mixed for about one hour. The shampoo comprising the controlled release system of the present invention was prepared by weighting into a jar 3.3 grams of the encapsulated fragrance of example 2 and 96.7 grams of the unfragranced shampoo base.

Four hair swatches were washed with the shampoo sample comprising the controlled release system of Example 2 and four hair swatches were washed with the control sample comprising the neat fragrance.

Two of the hair swatches in each experimental set (two washed with the shampoo comprising the encapsulated fragrance and two washed with the control sample) were dried using a blow dryer. The intensity of the fragrance retained on the wet swatches and the odor emitted 1 minute after drying the hair with a blow dryer was evaluated using a scale of 1 to 10, where 1 measures a low odor intensity and odor intensity of 10 measures a high intensity, pleasant odor. Odor perception is, by its nature, a very subjective determination and therefore needs to be determined by a panel of trained odor evaluator. According to the procedure, the hair swatches tested were provided to a panel of six odor evaluators who independently rank odor intensity retained on the wet hair swatches and in the proximate environment, 1 minute after blow drying the hair. The odor evaluation results were as follow:

| | Wet Hair | One Minute After Blow-Drying |
|---|---|---|
| Neat Fragrance (Control) | 3 | 4 |
| Encapsulated Fragrance | 4 | 8 |

These results show that the hair swatches washed with the control samples, comprising the neat fragrance, had very low odor intensity. The hair swatches washed with the shampoo comprising the encapsulated fragrance had higher odor intensity. Thus, the controlled release system of the present invention, adhere to hair and can be utilize to deposit higher level of fragrance onto hair. Only the hair swatches washed with the shampoo comprising the encapsulated fragrance provided high impact menthol "burst" upon blow drying the hair. Thus, the controlled release system of the present invention have the ability to provide heat triggered release of the active agents and yield high impact odor "burst" upon blow drying the hair or other type of heat treatment.

The other four hair swatches (washed with the shampoo comprising the encapsulated fragrance and the control sample) were air-dried and odor intensity of the fragrance retained on the dry swatches was evaluated after one hour and after 8 hours using the same scale as above. According to the procedure, the hair swatches to be tested were provided to a panel of six odor evaluators who independently rank odor intensity retained on the hair swatches. The odor evaluation results after one hour and after 8 hours, on the dry hair swatches were as follow:

|  | Neat Fragrance (Control) | Encapsulated Fragrance |
|---|---|---|
| One Hour | 4 | 7 |
| 8 Hours | 2 | 6 |

These results show that the hair swatches washed with the control samples, comprising the neat fragrance, had low odor intensity. The hair swatches washed with the shampoo comprising the encapsulated fragrance had higher odor intensity. Thus, the controlled release system of the present invention adheres to hair and can be utilize to deposit higher level of fragrance onto hair. Odor intensity of the hair swatches washed with the shampoo comprising the encapsulated fragrance, after 8 hours, was significantly higher than that of the swatches washed with these products comprising the neat fragrance. Also, Odor intensity of the hair swatches washed with the shampoo comprising the encapsulated fragrance after 8 hours remained almost the same as that after one hour. Thus, the controlled release system of the present invention have the ability to sustain the release of fragrance and provide extended release. The release rate of the fragrance, or other sensory markers, can be synchronize with that of the active agent to convey to the consumer the product performance.

What is claimed is:

1. A controlled release composition comprising:
   a plurality of solid nano-spheres, each of said solid nano-spheres comprising an effective amount of a first active agent and a cationic surface active agent, said plurality of nano-spheres are formed of a hydrophobic material, said plurality of nano-spheres being encapsulated within a pH sensitive or salt sensitive micro-sphere, said pH sensitive or salt sensitive micro-sphere is formed of a pH sensitive or salt sensitive matrix material wherein each of said nano-spheres has an average size of about 0.05 to about 2 microns and said micro-sphere has a size of from about 2 microns to about 50 microns.

2. The composition of claim 1 wherein said hydrophobic material is selected from one or more of the group consisting of natural wax, synthetic wax, vegetable wax, natural wax and silicon copolymer, synthetic wax and silicon copolymer, fatty acid esters, fatty alcohols, solid hydrogenated plant oil, natural polymers and synthetic polymers.

3. The composition according to claim 1 wherein said pH sensitive micro-sphere degrades or dissolves when said pH sensitive micro-sphere contacts a solution having a pH in the range of about 3 to about 12.

4. The composition according to claim 1 wherein said pH sensitive micro-sphere degrades or dissolves when said pH sensitive micro-sphere contacts a solution having a pH in the range of about 7 to about 9.

5. The composition according to claim 1 wherein a first portion of said plurality of nano-spheres are adhered to a second portion of said plurality of nano-spheres with a pH sensitive or salt sensitive matrix material.

6. The composition according to claim 1 wherein said pH sensitive material is formed of a copolymer of acrylate, styrene and maleic acid copolymers, formalized gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives, acrylic acid and acrylic ester copolymer, methacrylic acid and esters thereof vinyl acetate and crotonic acid copolymers.

7. The composition according to claim 1 wherein said pH sensitive material is formed of a copolymer having ionizable groups selected from the group consisting of polyphosphene, vinyl pyridine, vinyl aniline, polylysine, polyomithine, protein, and polymers with substituents containing amino moieties.

8. The composition according to claim 1 further comprising a moisture sensitive material mixed with said pH sensitive or salt sensitive material of said micro-sphere.

9. The composition according to claim 8 wherein said moisture sensitive material is selected from the group consisting of polyvinyl pyrrolidone, water soluble cellulose, polyvinyl alcohol, ethylene maleic anhydride copolymer, methyl vinyl ether maleic anhydride copolymer, polyethylene oxides, warer soluble polyamide, polyester, copolymers or homopolymers of acrylic acid, polyacrylic acid, polystyrene acrylic acid copolymer, starch derivatives, polysaccharide, hydrocolloid, natural gum, protein, and mixtures thereof.

10. The composition of claim 9 wherein said polyvinyl alcohol has a degree of hydrolysis from about 75% to about 99%.

11. The composition according to claim 1 wherein said cationic surface active agent is selected from the group consisting of cationic quatemary ammonium salts, acrylic quatemary ammonium salts having at least two $C_{8-30}$ alkyl chains;
   diamido quatemary ammonium salts, biodegradable quatemary ammonium salts and tertiary fatty amines having at least one $C_8$ to $C_{30}$ alkyl chains.

12. The composition according to claim 1 wherein said cationic surface active agent is selected from the group consisting of ditallowdimethyl ammonium methylsulfate, di(hydrogenated tallow)dimethyl ammonium methylsulfate, distearyldimethyl ammonium methylsulfate, dicocodimethyl ammonium methylsulfate, ditallowdimethyl ammonium methylsulfate, di(hydrogenated tallow)dimethyl ammonium methylsulfate, distearyldimethyl ammonium methylsulfate, dicocodimethyl ammonium methylsulfate, methyl-bis(hydrogenated tallow amidoethyl)-2-hydroxyethyl ammonium methyl sulfate, methyl bis(tallowamidoethyl)-2-hydroxypropyl ammonium methylsulfate, N,N-di tallowoyl-oxy-ethyl)-N,N,-dimethyl ammonium methyl sulfate and N,N-di (tallowoyl-oxy-propyl)-N, N-dimethyl ammonium methyl sulfate and tallow-di-methylamine and cyclic amines, 1-(hydrogenated tallow)amidoethyl-2-(hydrogenated tallow)imidazoline.

13. The composition according to claim 1 further comprising a cationic fabric conditioning agent selected from the group consisting of: behenyltrimethylammonium chloride; ditallowdimethylammonium methylsulfate; ditallowdimethylammonium chloride;
methyl(1) stearylamidoethyl(2) stearylimidazolinium methosulfate;
methyl(1)stearylamidoethyl(2)stearylimidazolinium chloride; N,N-di(tallowyl-oxy-ethyl)-N,N-dimethyl ammonium chloride; N,N-di(canolyl-oxy-ethyl)-N,N-dimethyl ammonium chloride;
N,N-di(tallowyl-oxy-ethyl)-N-methyl, N-(2-hydroxyethyl) ammonium chloride; N,N-di(canolyl-oxy-ethyl)-N-methyl, N-(2-hydroxyethyl) ammonium chloride; N,N-di(2-tallowyloxy-2-oxo-ethyl)-N,N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowoyloxy- 2-ethyl)-N-(2-tallowyloxy-2-oxo-ethyl)-N,N-dimethyl ammonium chloride; N-(2-canolyloxy-2-ethyl)-N-(2-canolyloxy-2-oxo-ethyl)-N,N-dimethyl ammonium chloride; N,N,N-tri (tallowyl-oxy-ethyl)-N-methyl ammonium chloride; N,N,N-tricanolyl-oxy-ethyl)-N-methyl ammonium chloride; N-(2-tallowyloxy-2-oxoethyl)-N-(tallowyl)-N,N-dimethyl ammonium chloride; N-(2-canolyloxy-2-oxoethyl)-N-(canolyl)-N,N-dimethyl ammonium chloride; 1,2-ditallowyloxy-3 -N,N,N-trimethylammoniopropane chloride; and 1,2-dicanolyloxy-3 -N,N,N-trimethylammoniopropane chloride; and mixtures of thereof.

14. The composition according to claim 1 wherein said first active agent is a fragrance.

15. The composition of claim 14 wherein said first active agent further comprises a conditioner selected from the group consisting of mineral oil, petrolatum, vegetable oils, soybean, maleated soybean oil, dimethicone, dimethicone copolyol, cationic monomers and polymers, guar hydroxypropyl trimonium chloride, distearyl dimethyl ammonium chloride and combinations thereof.

16. The composition of claim 1 wherein said first active agent is present in about 1% to about 80% by weight of said nano-spheres.

17. The composition of claim 1 wherein said pH sensitive matrix material is formed of a pH or salt sensitive material and polyvinyl alcohol in an amount of about 1% to about 50% by weight of the matrix material.

18. The composition of claim 1 wherein said pH sensitive matrix material is formed of a pH or salt sensitive material and about 1% to about 20% polyvinyl alcohol by weight of the matrix material and about 1% to about 20% polysaccharide by weight of the matrix.

19. The composition of claim 1 wherein said first active agent is released upon heat treatment of said nano-spheres.

20. The composition according to claim 1 wherein said composition comprises a free flowing powder.

21. A controlled release composition comprising:
a plurality of solid nano-spheres, each of said solid nano-spheres comprising an effective amount of a first active agent, and a cationic surface active agent said plurality of nano-spheres are formed of a hydrophobic material, said plurality of nano-spheres being encapsulated within a pH sensitive or salt sensitive micro-sphere, said pH sensitive or salt sensitive micro-sphere is formed of a pH sensitive or salt sensitive matrix material, and a second active agent encapsulated in said pH sensitive or salt sensitive matrix material wherein said pH sensitive or salt sensitive matrix material releases said second active agent upon contact with a solution having a predetermined pH in the range of about 3 to about 12 wherein each of said nano-spheres has an average size of about 0.05 to about 2 microns and said micro-sphere has a size of from about 2 microns to about 50 microns.

22. The composition according to claim 21 wherein said pH or salt sensitive material upon contact with said solution releases said second active agent to provide a burst and said first active agent is released continuously thereafter for an extended period of time.

23. The composition according to claim 22 wherein the extended period of time is in the range of a day to a period of a few weeks.

24. A controlled release composition comprising:
a plurality of solid nano-spheres, each of said solid nano-spheres comprising an effective amount of a first active agent, said plurality of nano-spheres are formed of a hydrophobic material, said plurality of nano-spheres being encapsulated within a pH sensitive or salt sensitive micro-sphere, said pH sensitive or salt sensitive micro-sphere is formed of a pH sensitive or salt sensitive matrix material, a cationic charge booster within said solid nano-sphere wherein each of said nano-spheres has an average size of about 0.05 to about 2 microns and said micro-sphere has a size of from about 2 microns to about 50 microns.

25. The system of claim 24 wherein said cationic charge booster is selected from the group consisting of a quaternary ammonium compound, polyvinyl amine, polyalkyleneimine, polyethyleneimine, and a poly-quaternary ammonium compound.

26. A fragrance carrier system comprising a composition comprising a plurality of solid nano-spheres including a fragrance and a cationic conditioning agent are formed of a hydrophobic material, said plurality of nano-spheres being encapsulated within a pH sensitive or salt sensitive micro-sphere, said pH sensitive or salt sensitive micro-sphere is formed of a pH sensitive or salt sensitive matrix material wherein each of said nano-spheres has an average size of about 0.05 to about 2 microns and said micro-sphere has a size of from about 2 microns to about 50 microns.

27. A fabric care product comprising the fragrance carrier system of claim 26.

28. The fabric care product of claim 27 wherein said product further comprises ironing aid, silicones, anti-shrinkage agent, anti-wrinkle agent, fabric crisping agent, spotting agent, germicide, fungicide, stabilizer, preservative, bactericide, flow agent, and mixtures thereof.

29. A method for forming a controlled release composition, said composition comprising:
a plurality of solid nano-spheres, each of said solid nano-spheres comprising an effective amount of a first active agent, comprising a fragrance said plurality of nano-spheres are formed of a hydrophobic material, said plurality of nano-spheres being encapsulated within a pH sensitive or salt sensitive micro-sphere, said pH sensitive or salt sensitive micro-sphere is formed of a pH sensitive or salt sensitive matrix material, a second active agent encapsulated in said pH sensitive or salt sensitive matrix material wherein said pH sensitive or salt sensitive matrix material releases said second active agent upon contact with a solution having a pH in the range of about 3 to about 12 wherein said nano-spheres are formed of a hydrophobic material comprising the steps of:

heating said hydrophobic material to a temperature above the melting point to form a hot melt;

dissolving or dispersing said first active agent into the melt;

dissolving or dispersing said second active agent, and said pH or salt sensitive matrix material, in an aqueous phase and heating it to above the melting temperature of said hydrophobic material;

mixing the hot melt with said aqueous phase to form a dispersion;

high shear homogenization of the dispersion at a temperature above the melting temperature until a homogeneous fine dispersion is formed;

cooling the dispersion to ambient temperature to form an emulsified mixed suspension; and spray drying the emulsified mixed suspension to form a dry powder composition.

* * * * *